United States Patent [19]

Pesterfield, Jr.

[11] Patent Number: 5,708,036
[45] Date of Patent: Jan. 13, 1998

[54] METHOD OF TREATING PREMATURE UTERINE CONTRACTIONS USING THE OPTICALLY ACTIVE R(−)-ISOMER OF ALBUTEROL

[76] Inventor: E. Charles Pesterfield, Jr., 1640-22 Powers Ferry Rd., Marietta, Ga. 30067

[21] Appl. No.: 592,988

[22] Filed: Jan. 29, 1996

[51] Int. Cl.⁶ .................................................. A61K 31/135
[52] U.S. Cl. ........................... 514/653; 514/649; 514/935
[58] Field of Search ................................. 514/653, 935, 514/649

[56] References Cited

U.S. PATENT DOCUMENTS 5,164,189  11/1992  Faradieh et al. .................. 424/448
5,290,561   3/1994  Faradieh et al. .................. 424/449
5,362,755  11/1994  Barberich et al. ................. 514/649

*Primary Examiner*—Marianne M. Cintins
*Assistant Examiner*—M. Moezie
*Attorney, Agent, or Firm*—Deveau, Colton & Marquis

[57] ABSTRACT

The optically pure R-isomer of the adrenergic beta-2 agonist albuterol, substantially free of its corresponding S-isomer, has been found to potently inhibit premature uterine contractions in female subjects, suffering from said condition, while avoiding side effects associated with the corresponding S-isomer. A new method is disclosed utilizing the optically pure R(−)-isomer of albuterol for treating premature uterine contractions while minimizing the side effects associated with administration of racemic albuterol.

10 Claims, No Drawings

METHOD OF TREATING PREMATURE UTERINE CONTRACTIONS USING THE OPTICALLY ACTIVE R(–)-ISOMER OF ALBUTEROL

BACKGROUND OF THE INVENTION

Many biologically active molecules exist as enantiomers. Although structurally identical, enantiomers can have different effects in biological systems: one enantiomer may have specific therapeutic activity while the other enantiomer may have no therapeutic activity or may have entirely different forms of biological activity.

The form in which adrenergic beta-2 agonists presently are used are as racemic mixtures of two isomer (ex. R- and S-albuterol; R- and S-terbutaline). An R-isomer of a racemic compound is structurally identical to the S-isomer and structurally the isomers differ only in that one isomer is a mirror image of the other.

The therapeutic action of beta-2 adrenergic drugs is to activate adrenergic beta-2 receptors and thereby initiate cellular responses, the most well-known is the relaxation of bronchial smooth muscles. Thus beta-2 agonists are most commonly used to treat bronchial spasms associated with asthma. These drug have also been used to inhibit premature contractions (labor) of the pregnant uterus, but there are potentially hazardous side effects of the drug when used for this indication, and prevention of premature labor has not been an officially approved indication in most countries, including USA. The potentially hazardous side effects include induction of uterine hyperreactivity (stimulation of uterine contractions) and teratogenic effects of the drug to the fetus.

SUMMARY OF THE INVENTION

The present invention relates to a method of inhibiting premature uterine contractions in a pregnant female individual, by administering the pure R-isomer of albuterol, which relaxes uterine smooth muscle, while eliminating side effects caused by S-albuterol. The method is particularly useful in treating subjects that have demonstrated a propensity for premature uterine contractions, induced by known or unknown causes. In cases where there is a risk for premature uterine contractions, it is important to have a tocolytic medication that does not further facilitate uterine contractions. Also, the medication should not cause harm to the fetus and should not exhibit other adverse side. A composition containing pure R-albuterol is particularly useful for this application because R-albuterol has now been found to exhibit these desired characteristics. The present method provides a safe, effective method for treating premature uterine contractions while reducing undesirable side effects, for example tremor, nervousness, shakiness, dizziness, increased appetite, cardiac tachycardia of the fetus and particularly uterine hyperreactivity, associated with beta-adrenergic drugs. In addition to the above, racemic albuterol may also cause teratogenic effects, which are believed to be associated with the S-isomer. Administration of pure R-albuterol eliminates any teratogenic activity that is associated with the S-isomer. Importantly, administration of the pure R-isomer also eliminates premature contractions of the uterine smooth muscle while avoiding the uterine hyperreactivity that is induced by the S-isomers of this beta-2 agonist.

DETAILED DESCRIPTION OF THE INVENTION

The present invention relies on the tocolytic activity of the R(–)-isomer of albuterol to provide relief from premature uterine contractions, while simultaneously eliminating uterine hyperreactivity, caused by the S-isomer in racemic albuterol. Simultaneously other side effects that are caused by the S-isomer—ex. bronchial hyperreactivity induced by S-albuterol in asthmatic subjects—are eliminated by using the pure R-isomer in stead of the racemic mixture. Also side effects that may reside in both isomers will be reduced by using the pure R-isomer in stead of the racemate. In the present method, the optically pure R-isomer of albuterol, substantially free of the S-isomer, is administered alone, or in combination with one or more other drugs in adjunctive treatment, to an individual in whom relief from uterine contractions is desired. The R-isomer of albuterol as used herein refers to the optically pure R(+)-isomer of α1[(tert-butylamino)methyl]-4-hydroxy-m-xylene-a,a'-diol, and to any biologically acceptable salt or ester thereof. The term "optically pure" or "substantially free of the S-enantiomer" as used herein means that the composition contains at least 85% by weight of the R-isomer of a beta-agonist and 15% by weight or less of the S-isomer. Optically pure adrenergic beta-agonists are readily obtainable by methods known to those skilled in the art, for example, by synthesis from an optically pure intermediate or resolution of the racemic compound into its isomers.

In the present method; the R-isomer of albuterol is administered to an individual, who suffers from premature contractions of uterine smooth muscle. For example, R-albuterol is administered to an individual after the onset of premature uterine contractions to reduce or eliminate said contractions. In another embodiment, the optically pure R-isomer of albuterol is administered prophylactically to prevent the occurrence of uterine contractions or to reduce the extent to which they may occur.

In the present method, the optically active R-isomer of albuterol can be administered by inhalation, parenterally, subcutaneously, intravenously, intramuscularly or other injection or infusion, orally, sublingually, topically, transdermally, vaginally, rectally or via an implanted reservoir containing the drug. The form in which the drug will be administered (e.g. inhalant, powder, tablet, capsul, solution, emulsion etc.) will depend on the route by which it is administered. The quantity of the drug to be administered will be determined on an individual basis, and will be based on the pharmacological potency of the drug, the route of administration and at least in part in consideration of the individual's size, the severity of the symptoms to be treated and the results sought. In general, quantities of optically pure R-albuterol sufficient to eliminate the premature uterine contractions will be administered. The actual dosage (quantity administered at a time) and the number of administrations per day will depend on the pharmacokinetic property of the drug and the mode of drug administrations, for example, by inhaler, nebulizer or oral administration. For example about 10 to 3000 micrograms of the optically pure R(–)-isomer of albuterol may be given by various forms of inhalation devices (metered dose inhalers, dry powder inhalers, nebulizers etc.), 1 to 50 milligrams may be given by the oral route (tablets, caplets, controlled release formulations, sublingual formulations, etc.) once or more times per day may be adequate in most individuals to produce the desired effect. For oral administration of R-albuterol, e.g. tablet or syrup, a dose of about 1 mg to about 15 mg one to four times daily is administered to produce the desired effect. Drug administration may take place more frequently as determined by the caring physician. Controlled-release, sustained-released or delayed-released formulations of R-albuterol, containing 4 mg to 50 mg may be used to obtain controlled, sustained, or delayed therapeutic effect.

In the method of the present invention, the optically pure R-isomer of albuterol can be administered together with one or more other compound(s). For example, various uterospasmolytic drugs such as anticholinergic drugs, leucotriene antagonists, lipoxygenase inhibitors, antihistaminergic drugs, antiserotonergic drugs, PAF-antagonists, thromboxane antagonists, thromboxane synthetase inhibitors or adrenergic beta-2 stimulators can be given with or between the doses of R-albuterol. Thus R-albuterol can be combined with a longacting beta-agonist (ex R-salmeterol). Compounds that improve or prolong the therapeutic effect of R-albuterol, e.g. compounds that inhibit its metabolic degradation (ex. acetaminophen), may also be co-administered to patients given R-albuterol. The two (or more) drugs (the optically pure active isomer of albuterol, together with the other drug(s)) can be administered in one composition or as separate entities. For example they can be administered in a single capsule, tablet, powder, or liquid, mist, aerosol, injection, transdermal delivery system, etc. or as individual drug formulations. The components included in a particular formulation, in addition to optically pure R-albuterol and another drug or drugs, are determined primarily by the manner in which the composition is to be administered. For example, a composition to be administered in inhalant form can include, in addition to the drug(s), a liquid carrier and/or propellant. A formulation to be administered in tablet form can include a filler (e.g., lactose), a binder (e.g., carboxymethyl cellulose, gum arabic, gelatin), an adjuvant, a flavoring agent, a coloring agent and a coating material (e.g., wax or a plasticizer). A formulation to be administered in liquid form can include the combination of drugs and, optionally, an emulsifying agent, a flavoring agent and/or a coloring agent. A composition to be administered vaginally or rectally may include the combination of drugs consisting of R-albuterol and for example at least one additional drug selected from the group consisting of smooth muscle relaxants, antihistamines, antiserotonergics, anticholinergics and metabolic inhibitors.

In general, according to the method of the present invention, the optically pure R-albuterol, alone or in combination with another drug(s), is administered to an individual, periodically or continuously as necessary to inhibit or reduce uterine contractions.

The present composition and method provide effective tocolytic treatment while minimizing the undesired side effects associated with the use of racemic albuterol. These side effect include central nervous system effects such as tremor, shakiness, dizziness and increased appetite, and cardiac effects such as fetal tachycardia and uterine contractions, induced by racemic albuterol. In addition, teratogenic effects associated with racemic albuterol are believed to reside in the S-isomer of the drug. Thus, by the administration of the pure R-isomer of albuterol, the teratogenic effects and the uterine contractile effects of the corresponding S-isomer will be avoided.

EQUIVALENTS

Those skilled in the art will recognize, or be able to ascertain, using no more than routine experimentation, many equivalents to the specific embodiments of the invention described herein. Such equivalents are intended to be encompassed in the scope of the following claims.

I claim:

1. A method of preventing or treating premature uterine contractions in an individual with the R-isomer of albuterol or a pharmaceutically acceptable salt thereof, while reducing side effects associated with administration of the corresponding racemic drug or with the corresponding S-isomer, comprising acutely or chronically administering to an individual, a quantity of said R-isomer or of a pharmaceutically acceptable salt thereof sufficient to result in the reduction or the elimination of premature uterine contractions while simultaneously eliminating or reducing undesirable side effects residing in the corresponding S-isomer, said R-isomer of albuterol or salt thereof being substantially free of its S-isomer.

2. A method of claim 1 wherein the optical purity of the R-isomer of albuterol is greater than approximately 85% by weight.

3. A method of claim 1 wherein the optical purity of the R-isomer of albuterol is greater than 99% by weight.

4. A method of claim 1, wherein said administration is by inhalation of from approximately 10 micrograms to approximately 5000 micrograms of the R-isomer of albuterol or its pharmaceutically acceptable salt one to four times daily.

5. A method of claim 1, wherein said administration is oral administration of from approximately 1 milligram to approximately 50 milligrams of the R-isomer of albuterol or its pharmaceutically acceptable salt one to four times daily.

6. A method of claim 1, wherein said administration is transdermal administration of from approximately 1 milligram to approximately 100 milligrams of the R-isomer of albuterol or its pharmaceutically acceptable salt daily.

7. A method of preventing or treating premature uterine contractions in an individual with R-albuterol or its pharmaceutically acceptable salt, while reducing side effects associated with administration of racemic albuterol, comprising administering to the individual a quantity of R-albuterol or its pharmaceutically acceptable salt, substantially free of its S-isomer, sufficient to result in the relaxation of the uterus while simultaneously reducing undesirable side effects, in combination with at least one additional drug selected from the group consisting of smooth muscle relaxants, antihistamines, antiserotonergics, anticholinergics, leucotriene antagonists, lipoxygenase inhibitors, PAF-antagonists, thromboxane antagonists and metabolic inhibitors.

8. The method of claim 1, wherein said administration is sublingual.

9. The method of claim 1, wherein said administration is intravenous.

10. The method of claim 1, wherein said administration is intravaginal.

* * * * *